United States Patent [19]

Chang et al.

[11] Patent Number: 6,162,757
[45] Date of Patent: Dec. 19, 2000

[54] ACID CATALYST COMPOSITION

[75] Inventors: Clarence D. Chang, Princeton; Scott Han, Lawrenceville, both of N.J.; Scott A. Stevenson, Houston, Tex.; James C. Vartuli, West Chester, Pa.

[73] Assignee: Mobil Oil Corporation, Fairfax, Va.

[21] Appl. No.: 09/357,546

[22] Filed: Jul. 20, 1999

[51] Int. Cl.$^7$ ................ B01J 21/06; B01J 23/10
[52] U.S. Cl. ............ 502/302; 502/303; 502/304; 502/349; 502/350
[58] Field of Search ................ 502/302, 303, 502/304, 349, 350

[56] References Cited

U.S. PATENT DOCUMENTS

| | | | |
|---|---|---|---|
| 4,212,766 | 7/1980 | Brazdil et al. | 568/476 |
| 5,113,034 | 5/1992 | Soled et al. | 585/510 |
| 5,145,587 | 9/1992 | Ishii et al. | 210/759 |
| 5,345,026 | 9/1994 | Chang et al. | 585/700 |
| 5,382,731 | 1/1995 | Chang et al. | 585/315 |
| 5,510,309 | 4/1996 | Chang et al. | 502/308 |
| 5,888,464 | 3/1999 | Wu et al. | 423/213.5 |
| 5,898,014 | 4/1999 | Wu et al. | 502/302 |
| 5,945,370 | 8/1999 | Yokoi et al. | 502/304 |
| 5,962,367 | 10/1999 | Shen et al. | 502/439 |

FOREIGN PATENT DOCUMENTS 288339 11/1989 Japan .

OTHER PUBLICATIONS

K. Arata and M. Hino, "Synthesis of Solid Superacid of Tungsten Oxide Supported On Zirconia and Its Catalytic Action", Proceedings 9$^{th}$ International Congress on Catalysis, vol. 4, pp. 1727–1735 (1988) no month available.

Leitenburg et al., "A Novel and Simple Route to Catalysts with a High Oxygen Storage Capacity: the Direct Room–temperature Synthesis of CeOz–ZrOz Solid Solutions" pp. 2181–2182 (1995) no month available.

S. Meriani, "Features of the Caeria–Zirconia System*", Materials Science and Engineering, A109, pp. 121–130 (1989) no month available.

A. Trovarelli, "Catalytic Properties of Ceria and $C_eO_2$–Containing Materials", Cat. Reviews, 38(4), pp. 440–520 (1996) no month available.

T. Yamaguchi, N. Ikeda, H. Hattori, and K. Tanabi, "Surface and Catalytic Properties of Cerium Oxide", Journal of Catalysis, 67, 324–330(1981) no month available.

S. Sugunan, G. Chemparathy, A. Paul, "Acid base characteristic of binary oxides of Zr with Ce and La", Indian Journal of Engineering & Material Science, vol. 3, pp. 45–47, (1996) no month available.

*Primary Examiner*—Elizabeth D. Wood

[57] ABSTRACT

A novel synthesis composition of a solid acid containing zirconium, in addition to a rare earth element, such as cerium, has the potential for catalytic conversions of hydrocarbons, especially for isomerization of paraffins, ring opening of cyclics, hydrocracking, alkylation, hydrogenation of polynuclear aromatics, selective catalytic reduction of nitrogen oxides, and oligomerization of light olefins.

5 Claims, No Drawings

ACID CATALYST COMPOSITION

FIELD OF THE INVENTION

This invention is concerned with the preparation of high activity solid acid catalysts which comprise oxides of lanthanides (rare earth elements), such as cerium, in addition to a Group IVB metal, such as zirconium. This catalyst is particularly suited for paraffin isomerization.

BACKGROUND

Strongly acidic mixed metal oxide catalysts have shown potential for a variety of hydrocarbon processes. Such catalysts often comprise an oxide of a Group IVB metal, preferably zirconia or titania, which has been modified with an oxyanion of a Group VIB metal, such as an oxyanion of tungsten, e.g. tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in Proceedings 9th International congress on Catalysis, volume 4, pages 1727–1735 (1988), the entire disclosures of these publications are expressly incorporated herein by reference. According to these publications, tungstate is impregnated onto a preformed solid zirconia material.

For the purposes of the present disclosure, the expression, Group IVB metal oxide modified with an oxyanion of a rare earth metal, is intended to connote a material comprising, by elemental analysis, a Group IVB metal, a rare earth metal and oxygen, having more acidity than a simple mixture of separately formed Group IVB metal oxide mixed with a separately formed rare earth metal oxide or oxyanion. Actual chemical interaction occurs between a source of a Group IVB metal oxide and a source of a rare earth metal oxide or oxyanion.

The generation of acid activity in solid acid catalysts in general, and in the tungsten/zirconia based catalyst specifically, can require the calcination/activation of the catalyst at temperatures up to about 800° C. This extreme temperature requirement causes significant loss of catalyst surface area and increases difficulties in catalyst manufacture. It has been reported that calcination temperatures greater than 700° C. are required to generate superacid activity in the $WO_x/ZrO^2$ system.

Maximum activity was observed when calcination was carried out in the temperature range of 800 to 850° C. (K. Arata and M. Hino, Proceedings, 9th International Congress on Catalysis, Calgary, Canada, 1727, 1988). Recently, it was discovered (see Ser. No. 08/728,395, incorporated by reference) that the addition of a noble metal component to the $WO_x/ZrO_2$ material produces a superior catalyst for hydrocarbon processing. Various process applications of this metal-modified $WO_x/ZrO_2$ catalyst have been described U.S. Pat. Nos. 5,345,026 and 5,382,731. U.S. Pat. No. 5,510,309 discloses a method of preparation for $WO_x/ZrO_2$ catalysts which is suitable for use in the instant invention. More recently, it has been found, as described in Ser. No. 08/332,169, now abandoned, that the addition of Fe and/or Mn has a positive effect on the catalytic activity of the noble metal-containing $WO_x/ZrO_2$ catalyst.

Mixed metal oxide catalysts containing cerium, a rare earth metal, have been used for a number of applications such as for oxygen storage in automobile exhaust catalysts (C. de Leitenburg, A. Trovarelli, F. Zamar, S. Maschio, G. Dolcetti, and J. Llorca, *J. Chem. Soc.*, Chem Commun., 2181, 1995) and in ceramics as solid electrolytes (S. Meriani, *Materials Science and Engineering*, A 109, 121–130, 1989). A recent review of the catalytic properties of ceria and ceria containing materials can be found in (A. Trovarelli) Cat. Reviews, 38(4), 440–520, 1996. Most of the catalytic applications are those of selective oxidation. The isomerization of 1-butene was noted (T. Yumaguchi, N. Ikeda, H. Hattori, and K. Tanabe, J. Catal., 67, 324, 1981).

Cerium has been also used with zirconia as an additive (~1–2%) to stabilize surface area and the tetragonal crystalline phase. A recent article (S. Sugunan, G. V. Chemparathy, and A. Paul, *Indian Journal of Engineering & Materials Sciences*, 3, 45–47, 1996) discussed the acid/base characteristics of ceria/zirconia mixed metal oxide combinations using Hammett indicators to measure the strength of the acid and base sites. The authors showed that ceria alone is basic; but in combination with various amounts of zirconia, acidity is developed. They synthesized various combinations ranging from pure ceria to pure zirconia in increments of 20 weight %. The maximum acidity was at a 60/40 $ZrO_2/CeO_2$ weight mixture activated at ~800° C. The Hammett value was $H_0$~-4.8 to 7.8. This value is not as acidic as 100% $H_2SO_4$ (-12), $WO_x/ZrO_2$ (-14.5) or $SO_4^-/ZrO_2$ (-16) obtained from Arata—Advances in Catalysis, 37, 165–211 (1990). However, initial isomerization data suggests that the acidity present on the catalyst preparation of the instant invention was significantly stronger. The initial preparation was a 5 weight percent ceria on zirconia catalyst which was calcined at 700° C.

SUMMARY

Solid acid catalysts which comprise oxides of zirconium in addition to a rare earth metal or metals (lanthanides), such as cerium, produce an active catalyst for paraffin isomerization. The presence of a rare earth metal provides for the generation of acid sites at lower activation temperatures than are required for other mixed metal oxide catalysts, such as those employing tungsten/zirconia based materials. Furthermore, the usefulness of these catalysts in the area of paraffin isomerization has been heretofore unknown. These catalysts are also useful in the areas of ring opening of cyclics, hydrocracking, alkylation, hydrogenation of polynuclear aromatics, selective catalytic reduction of nitrogen oxides, and oligomerization of light olefins.

DESCRIPTION OF THE PREFERRED EMBODIMENT

Suitable sources of Group IVB metal oxide, used for preparing the present catalyst, include compounds capable of generating such oxides, such as oxychlorides, chlorides, nitrates, oxynitrates, etc., particularly of zirconium Alkoxides of such metals may also be used as precursors or sources of the Group IVB metal oxide. Examples of such alkoxides include zirconium n-propoxide and titanium i-propoxide. The expression, hydrated zirconia, is intended to connote materials comprising zirconium atoms covalently linked to other zirconium atoms via bridging oxygen atoms, i.e., Zr—O—Zr, further comprising available surface hydroxyl groups. When hydrated zirconia is impregnated with a suitable source of metal oxide containing cerium under sufficient conditions, these available surface hydroxyl groups are believed to react with the source of metal oxide containing cerium to form an acidic catalyst. As suggested in the aforementioned article by K. Arata and M. Hino in Proceedings 9th International Congress on Catalysis, volume 4, pages 1727–1735 (1988), precalcination of Zr(OH)4 at a temperature of from about 100° C. to about 400° C. results in a species which interacts more favorably upon impregnation therewith. This precalcination is believed to result in the condensation of ZrOH groups to form a polymeric zirconia species with surface hydroxyl groups. This polymeric species is referred to herein as a form of a hydrated zirconia.

Suitable sources for the oxyanion of the rare earth metal include $CeO_2$ and $Ce(NO_3)_3 6H_2O$.

The present modified oxide material may be prepared by combining a first liquid solution comprising a source of a Group IVB metal oxide with a second liquid solution comprising a source of an oxyanion of a rare earth metal. This combination of two solutions takes place under conditions sufficient to cause co-precipitation of the modified oxide material as a solid from the liquid medium. Alternatively, the source of the Group IVB metal oxide and the source of the oxyanion of the rare earth metal may be combined in a single liquid solution.

This solution may then be subjected to conditions sufficient to cause co-precipitation of the solid modified oxide material, such as by the addition of a precipitating reagent to the solution. Water is a preferred solvent for these solutions.

The temperature at which the liquid medium is maintained during the co-precipitation may be less than about 200° C., e.g., from about 0° C. to about 200° C. This liquid medium may be maintained at an ambient temperature (i.e., room temperature) or the liquid may be cooled or heated. A particular range of such temperatures is from about 50° C. to about 100° C.

The liquid medium from which the present catalyst components are co-precipitated may optionally comprise a solid support material, in which case the present catalyst may be coprecipitated directly onto the solid support material. Examples of such support materials include the material designated M41S, which is described in U.S. Pat. No. 5,102,643. A particular example of such an M41S material is a material designated MCM-41, which is described in U.S. Pat. No. 5,098,684.

Support materials and/or co-catalyst materials may also, optionally, be co-precipitated from the liquid medium along with the Group IVB metal oxide and the oxyanion of the rare earth metal. An example of a co-catalyst material is a hydrogenation/dehydrogenation component such as Pt.

The modified acidic oxide may be contacted with hydrogen at elevated temperatures. These elevated temperatures may be 100° C. or greater, e.g., 250° C. or greater, e.g., about 300° C. The duration of this contact may be as short as one hour or even 0.1 hour. However, extended contact may also be used. This extended contact may take place for a period of 6 hours or greater, e.g., The optional components may also be co-precipitated along with the other components of the modified oxide material.

The present modified oxide material may be recovered by filtration from the liquid medium, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.1–24 hours, and more preferably for about 1.0–10 hours. In a most preferred embodiment, calcination is carried out at about 800° C. for about 1 to about 3 hours. The optional components of the catalyst (e.g., Group VIII metal, Group VIIB metal, etc.) may be added after or before the calcination step by techniques known in the art, such as impregnation, co-impregnation, co-precipitation, physical admixture, etc. The optional components, e.g., the hydrogenation/dehydrogenation component, may also be combined with the remaining catalyst components before or after these remaining components are combined with a binder or matrix material as described hereinafter.

The present catalyst is acidic and may be observed as being highly acidic, even to the extent of being a superacid. For example, this catalyst, whether analyzed in the presence or absence of optional components (e.g., hydrogenation/dehydrogenation components) and/or binder materials, may have an acid strength of a superacid as measured by the color change of an appropriate indicator, such as the Hammett indicator. More particularly, the Ho acid strength of the present catalyst may have a value of less than—13, i.e., an "acid strength" of greater than—13. The use of Hammett indicators to measure the acidity of solid superacids is discussed in the Soled et al. U.S. Pat. No. 5,157,199. This Soled et al. patent also describes the Ho acid strength for certain sulfated transition metal superacids.

The catalyst described herein may be used as a catalyst for isomerizing $C_4$ to $C_8$ paraffins. Suitable feeds contain substantial amounts of normal and/or singly branched low octane $C_4$ to $C_8$ hydrocarbons. The feed may also contain appreciable amounts of $C_6$ and $C_7$ cyclic paraffins which may undergo ring-opening reactions.

The present isomerization process may be carried out by contacting the hydrocarbon feed in either liquid or gas phase with the solid catalyst at temperatures less than 500° C., preferably less than 350° C., preferably less than 300° C., and at pressure in the range from 1 to 200 atmospheres, preferably from 1 to 100 atmospheres, more preferably 5 to 50 atmospheres. The isomerization process may be carried out either in the presence or absence of hydrogen, more preferably in the presence of hydrogen. The mole ratio of hydrogen to hydrocarbon is preferably in the range of 0.01:1 to 10:1.

It may be desirable to incorporate the present catalyst with another material to improve its properties. Such materials include active and inactive materials and synthetic or naturally occurring zeolites as well as inorganic materials such as clays, silica, and/or metal oxides.

The feedstock for the present process may be one which contains significant amounts of C5+normal and/or slightly branched paraffins. In addition, the feedstock may contain monocyclic aromatic compounds and/or cyclic paraffins, such as cyclohexane. Among the hydrocarbons having 6 or fewer carbon atoms in the feedstock, at least 1 wt. %, e.g., at least 5 wt. %, e.g., at least 10 wt. %, e.g., at least 20 wt. %, e.g., at least 30 wt. %, of these hydrocarbons may be cyclic hydrocarbons, e.g., aromatics or cyclic paraffins. Isomerization temperatures are suitably in the range of about 200° to 800° F. (about 93° to 425° C.); temperatures outside this range may be utilized although they are normally less preferred; temperatures from about 300° to 700° F. (about 149° to 370° C.) are typical. Pressures will normally be up to about 1000 psig (about 7,000 kPa abs.) although there is no reason why higher pressures should not be utilized. Lower pressures, in the range of about 50 to 600 psig (about 445 to 790 kPa abs.) may readily be employed and the use of relatively low pressures within this range will generally be preferred in order to permit the use of low pressure equipment. The isomerization is usually carried out in the presence of hydrogen, typically at a molar ratio relative to the feed from 0.01 to 10:1 and usually from 0.5:1 to 2:1. Space velocities are typically from 0.1 to 10 LHSV and usually from 0.5 to 5 LHSV. When an additional acidic material (Lewis acid or Bronsted acid) is included in the catalyst, lower operational temperatures may be used, favoring the isomerization over the less desired cracking reactions.

DATA

EXAMPLE 1

(Fe/W/Zr) Five hundred grams of $ZrOCl_2 \cdot 8H_2O$ were dissolved with stirring in 6.5 liters of distilled water. To this solution was added a mixture of 500 grams of distilled water and 7.5 grams of $FeSO_4 \cdot 7H_2O$. Finally a solution containing 263 grams of conc. $NH_4OH$, 500 mL of distilled $H_2O$, and 54 grams of $(NH_4)_6H_2W_{12}O_{40}V_xH_2O$ was added dropwise to the iron/zirconium solution over a 30–45 minute period. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of this catalyst was calcined to 830° C. in flowing air for 3 hours.

EXAMPLE 2

(Ce/Zr) 125 grams of $ZrO(NO_3)_2V_xH_2O$ were dissolved with stirring in 1.5 liters of distilled water. To the zirconyl nitrate solution a mixture of 10.3 grams of $Ce(NO_3)_3 \cdot 6H_2O$ and 2.3 grams of $(NH_4)_2SO_4$ dissolved in 100 ml of distilled water was added. A solution containing 40 grams of conc. $NH_4OH$ and 960 mL of distilled $H_2O$ was added dropwise over a 30–45 minute period. The pH of the final composite was adjusted to approximately 7 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of this catalyst was calcined 700° C. in flowing air for 3 hours.

Catalysts of Examples 1 and 2 were tested for pentane isomerization activity in a fixed bed down-flow reactor at 350 psig, 2 mole $H_2$/mole n-$C_5$, and 2 LHSV (cc n-$C_5$ feed per cc catalyst per hour). The catalysts were calcined at 500° C. for one hour under flowing air prior to catalytic testing. The results are shown in the table below. The data illustrates that the $Ce/ZrO_2$ catalyst demonstrate excellent isomerization activity comparable to the Fe-$WO_x/ZrO_2$ catalyst.

TABLE 1

Effect of catalyst composition on pentane isomerization activity

| composition | density (g/cm³) | surface area (m²/g) | i-$C_5$/(i + n) 375° F. | i-$C_5$/(i + n) 350° F. | $k_v$ @350° F. | $k_w$ @350° F. |
|---|---|---|---|---|---|---|
| Fe/$WO_x$/$ZrO_2$ | 1.17 | 60 | 0.732 | 0.650 | 2.93 | 1.56 |
| $CeO_x$/$ZrO_2$ | 1.80 | — | 0.723 | 0.682 | 3.46 | 1.21 |
| equilibrium | | | 0.755 | 0.761 | | |

We claim:

1. A method for preparing an acidic oxide catalyst having enhanced paraffin isomerization capability, which catalyst comprises a Group IVB metal oxide modified with an anion or oxyanion of a rare earth metal, said method comprising the steps of:

(a) coprecipitating a Group IVB metal oxide with an anion or oxyanion of a rare earth metal in the presence of an alkali material to produce a slurry containing said catalyst;

(b) steaming the slurry containing the catalyst;

(c) recovering the catalyst by filtration;

(d) washing the catalyst with water; and (e) calcining the catalyst.

2. The method according to claim 1, wherein the Group IV metal is zirconium and the rare earth metal is cerium.

3. The method according to claim 1, wherein the alkali material is ammonium hydroxide.

4. The method according to claim 1, wherein catalyst is calcined at a temperature of about 750° to 850° C.

5. The method according to claim 4, wherein the catalyst is calcined at about atmospheric pressure for about 1.0 to 10 hours.

* * * * *